United States Patent
Albert et al.

(10) Patent No.: US 10,625,236 B2
(45) Date of Patent: Apr. 21, 2020

(54) REACTOR WITH COOLING DEVICE

(71) Applicant: Siemens Aktiengesellschaft, Munich (DE)

(72) Inventors: Jakob Albert, Rathsberg (DE);
Manfred Baldauf, Erlangen (DE);
Jenny Reichert, Schwanfeld (DE);
Katharina Stark, Erlangen (DE);
Alexander Tremel, Möhrendorf (DE);
Peter Wasserscheid, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/086,763

(22) PCT Filed: Mar. 16, 2017

(86) PCT No.: PCT/EP2017/056247
§ 371 (c)(1),
(2) Date: Sep. 20, 2018

(87) PCT Pub. No.: WO2017/162513
PCT Pub. Date: Sep. 28, 2017

(65) Prior Publication Data
US 2019/0099734 A1   Apr. 4, 2019

(30) Foreign Application Priority Data
Mar. 22, 2016   (DE) .................. 10 2016 204 718

(51) Int. Cl.
*B01J 19/18*   (2006.01)
*B01J 8/02*   (2006.01)
*C07C 29/152*   (2006.01)

(52) U.S. Cl.
CPC ......... *B01J 19/1881* (2013.01); *B01J 8/0278* (2013.01); *B01J 8/0285* (2013.01);
(Continued)

(58) Field of Classification Search
CPC ........ B01J 8/0285; B01J 8/0278; B01J 8/009; B01J 19/1881; B01J 19/1893;
(Continued)

(56) References Cited

U.S. PATENT DOCUMENTS

| 2,411,760 A | * | 11/1946 | Sensel | B01J 8/0453 |
| | | | | 518/706 |
| 3,287,086 A | * | 11/1966 | Cahn | C01C 1/006 |
| | | | | 423/359 |

(Continued)

FOREIGN PATENT DOCUMENTS

| DE | 1301524 B | 8/1969 | ............... B01F 5/10 |
| WO | 2017/162410 A1 | 9/1917 | ............... B01J 8/00 |

(Continued)

OTHER PUBLICATIONS

International Search Report and Written Opinion, Application No. PCT/EP2017/054602, 8 pages, dated May 19, 2017.
(Continued)

*Primary Examiner* — Lessanework Seifu
(74) *Attorney, Agent, or Firm* — Slayden Grubert Beard PLLC

(57) ABSTRACT

Various embodiments may include a reactor comprising: a reaction chamber having a lower region defining a sorbent collection zone; a first feed device supplying reactants to the reaction chamber; a second feed device supplying a liquid sorbent to the reaction chamber; a discharge device connected to the sorbent collection zone for removing sorbent from the sorbent collection zone; and a cooling device for cooling the sorbent in the reaction chamber.

13 Claims, 2 Drawing Sheets

(52) U.S. Cl.
CPC ... *C07C 29/152* (2013.01); *B01J 2208/00168* (2013.01); *B01J 2219/00076* (2013.01)

(58) Field of Classification Search
CPC .... B01J 2219/00076; B01J 2208/00168; B01J 2208/00076
See application file for complete search history.

(56) References Cited

U.S. PATENT DOCUMENTS

| | | | | |
|---|---|---|---|---|
| 3,310,367 | A * | 3/1967 | Mavrovic | B01J 8/0278 422/202 |
| 3,471,424 | A * | 10/1969 | Tobin | B01J 19/1881 523/309 |
| 4,731,387 | A | 3/1988 | Westerterp | 518/706 |
| 4,790,915 | A | 12/1988 | Winsel et al. | 205/515 |
| 4,968,722 | A | 11/1990 | Westerterp | 518/706 |
| 5,712,313 | A | 1/1998 | Kramer et al. | 518/706 |
| 7,279,145 | B2 | 10/2007 | Balan | 422/239 |
| 7,470,825 | B2 * | 12/2008 | Lattner | B01D 3/009 568/909 |
| 2003/0086853 | A1 | 5/2003 | Devic | 423/272 |
| 2004/0033194 | A1 | 2/2004 | Amendola et al. | 48/61 |
| 2004/0048938 | A1 | 3/2004 | Mohedas et al. | 518/726 |
| 2007/0021514 | A1 | 1/2007 | Lattner | 518/726 |
| 2007/0248849 | A1 | 10/2007 | Preidel et al. | 429/437 |
| 2012/0027661 | A1 | 2/2012 | Shiflett et al. | 423/359 |

FOREIGN PATENT DOCUMENTS

| | | | | |
|---|---|---|---|---|
| WO | 2017/162513 A1 | 9/1917 | | B01J 19/18 |
| WO | 97/41953 A1 | 11/1997 | | B01J 10/00 |
| WO | 2009/106231 A1 | 9/2009 | | B01J 8/02 |
| WO | 2015/030578 A1 | 3/2015 | | C07C 29/152 |

OTHER PUBLICATIONS

International Search Report and Written Opinion, Application No. PCT/EP2017/056247, 10 pages, dated May 22, 2017.
European Office Action, Application No. 17709395.2, 6 pages, dated May 17, 2019.
U.S. Non-Final Office Action, U.S. Appl. No. 16/086,726, 13 pages, dated Apr. 15, 2019.
Australian Office Action, Application No. 2017238995, 4 pages, dated Aug. 1, 2019.

* cited by examiner

US 10,625,236 B2

REACTOR WITH COOLING DEVICE

CROSS-REFERENCE TO RELATED APPLICATIONS

This application is a U.S. National Stage Application of International Application No. PCT/EP2017/056247 filed Mar. 16, 2017, which designates the United States of America, and claims priority to DE Application No. 10 2016 204 718.3 filed Mar. 22, 2016, the contents of which are hereby incorporated by reference in their entirety.

TECHNICAL FIELD

The present disclosure relates to reactors. Various embodiments may include a reaction having a cooling device.

BACKGROUND

Conversion in chemical reactions is limited by the equilibrium position of the reaction. If the chemical equilibrium of a synthesis reaction lies only partly on the side of the products, a single-stage reaction regime results only in a partial conversion. If, on the other hand, the reaction products are removed from the reactor continuously, there is a continuous conversion of reactants to products within the reactor. For the continuous removal of reaction products, some systems employ sorbents. These sorbents form an additional phase which takes up selectivity products, which are thereby removed from the chemical equilibrium. The sorption phase can be discharged from the reactor together with the product.

SUMMARY

The teachings of the present disclosure may be embodied in a reactor and/or a method suitable for conducting equilibrium-limited reactions using a sorbent and at the same time increase the yield of reaction products relative to the prior art. For example, some embodiments may include a reactor having a reaction chamber (4), where at the reaction chamber (4) there is arranged a feed device (6) for reactants (7), a feed device for a liquid sorbent (9) and also a discharge device (10) for the sorbent (9), and where in a lower region of the reaction chamber there is a sorbent collection zone (12), characterized in that a cooling device (13) for cooling the sorbent (9) is provided.

In some embodiments, the cooling device (13) is arranged in the region of the sorbent collection zone (12).

In some embodiments, the cooling device (13) is arranged, in one operating state, below a liquid level (14) of the sorbent (9).

In some embodiments, a recycling device (16) for recirculating the sorbent (9) is arranged between the discharge device (10) and feed device (8).

In some embodiments, there is a circulating device (18) in the sorbent collection zone (12).

In some embodiments, there is a catalyst space (20) for accommodating a catalyst (22) in the reaction chamber (4).

In some embodiments, the reaction chamber (4) comprises the catalyst space (20) and a sorption space (24).

In some embodiments, the catalyst space (20) and the sorption space (24) are separated from one another by a gas-permeable element (26).

In some embodiments, the reactor (2) has a phase separator (28) which is arranged outside the reaction chamber (4) and is intended for separating the sorbent (9) from a reaction product (15), where the phase separator (28) is in communication with the discharge device (10).

In some embodiments, the phase separator (28) is part of the recycling device (16).

As another example, some embodiments may include a method for operating a reactor or implementing equilibrium-limited reactions, comprising method steps below, introducing reactants (7) into a reaction chamber (4), introducing a liquid sorbent (9) into the reaction chamber (4), where the reactants (7) are passed over a catalyst (22) located in the reaction chamber (4) and are converted to reaction products (15) over a catalyst surface until an equilibrium situation appears, where the reaction products (15) pass from the catalyst surface to the sorbent (9) and are absorbed by the latter, after which the sorbent (9') laden with the reaction products (15) settles in a sorbent collection zone, characterized in that the liquid sorbent (9, 9') in the reaction chamber is cooled by means of a cooling device.

In some embodiments, the sorbent (9, 9') is cooled by the cooling device (13) in the region of the sorbent collection zone (12).

In some embodiments, the sorbent (9') laden with the reaction product (15) is passed off out of the reaction chamber (4) and the reaction product (15) is separated from the sorbent (9'), and the sorbent (9) thus unladen is recycled by being reintroduced into the reaction chamber (4).

In some embodiments, the laden sorbent (9') is circulated by a circulating device (18) in the region of the sorbent collection zone (12).

BRIEF DESCRIPTION OF THE DRAWINGS

Further embodiments and further features such embodiments of the teachings herein are elucidated in more detail with reference to the following figures, in which.

DETAILED DESCRIPTION

Figure 1:
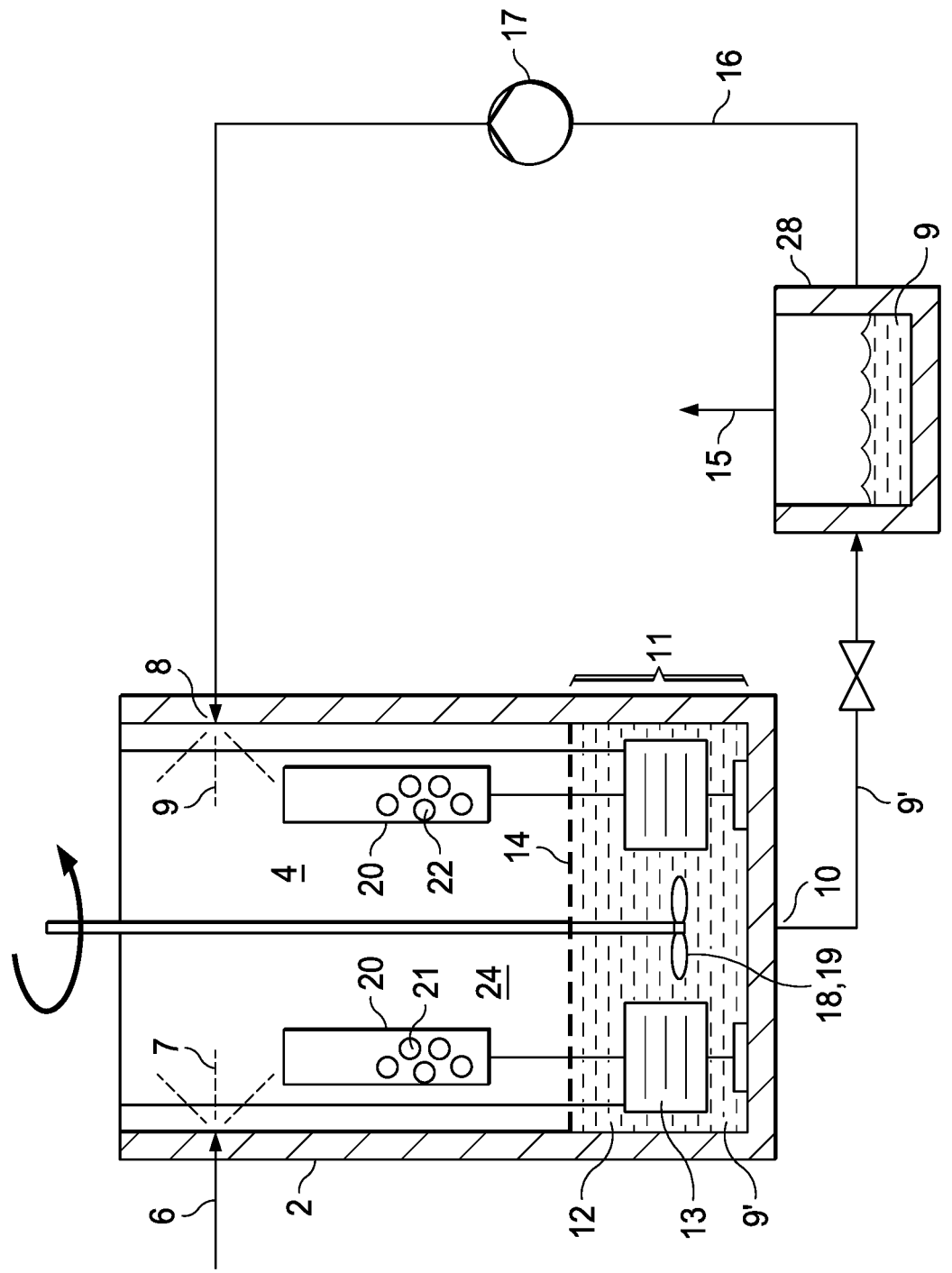
FIG. 1 shows a reactor having a reaction chamber and a sorbent collection zone, where the sorbent is cooled in the sorbent collection zone, according to the teachings herein.

In some embodiments, a reactor comprises a reaction chamber, where a feed device for reactants, a feed device for a liquid sorbent and also a discharge device for the sorbent are arranged at the reaction chamber. In a lower region of the reaction chamber here there is a sorbent collection zone, and the reactor is distinguished by the fact that there is a cooling device for cooling the sorbent. The effect of cooling the sorbent is on the one hand that thermal decomposition of the sorbent is prevented, in turn increasing the selection of possible sorbents and allowing the use of more efficient sorbents in the reaction. On the other hand, the cooling of the sorbent reduces the heating in the reaction chamber as a whole, with positive consequences for the equilibrium conversion of the reaction.

In some embodiments, the cooling device is arranged in the region of the sorbent collection zone. This results in effective cooling of the sorbent and in good heat transfer between the cooling device and the liquid sorbent medium.

In some embodiments, the cooling device is arranged so that in one operating state it lies below, or at least partially, a liquid level of the sorbent. As a result of this measure, optimum heat transfer from the cooling device to the sorbent is possible.

In some embodiments, a recycling device for recirculating the sorbent is arranged between the discharge device and the feed device. This recycling device is suitable for introducing the sorbent back into the reaction chamber; when the sorbent has already been cooled, this also has positive consequences for the stability during the reaction.

In some embodiments, a circulating device, more particularly a stirring device, is in the sorbent collection zone in order to ensure the exchange of heat between the sorbent and the cooling device.

In some embodiments, a catalyst space for accommodating a catalyst is in the reaction chamber, in order to accelerate the conversion reaction. The catalyst ensures that the reaction proceeds more rapidly, but does not substantially influence the equilibrium state. Reaction products which are at the catalyst surface are absorbed by the sorbent and led from the reaction chamber.

In some embodiments, the reaction chamber comprises the catalyst space and a sorption space. Separation of the catalyst material from the sorbent is useful with many pairings of catalyst and sorbent, since the two substances may influence one another adversely in respect of the reaction. In some embodiments, the sorption space and the catalyst space are separated from one another by a gas-permeable element. This element in turn is usefully impermeable to liquids or to drips of liquid. In this way, a gaseous reaction product is able to enter the sorption space from the catalyst space more easily, without sorbent present in liquid form being able to pass into the catalyst space. The element may be, for example, a woven fabric, more particularly a metallic woven fabric, or a selective membrane.

In some embodiments, the reactor comprises a phase separator which is arranged outside the reaction chamber and which serves to carry out separation between sorbent and the reaction product. In this case, this phase separator is in connection with the discharge device of the reactor. In some embodiments, this phase separator is part of the recycling device.

Some embodiments include a method for operating a reactor for implementing equilibrium-limited reactions. In some embodiments, the method comprises the following steps: first, a number of reaction reactants are introduced into a reaction chamber. Furthermore, a liquid sorbent is likewise introduced into the reaction chamber. The reactants here are passed over a catalyst which is located in the reaction chamber, and are converted therein into reaction products at the catalyst surface until an equilibrium situation occurs. The reaction products are passed from the catalyst surface to the sorbent and are absorbed by said sorbent, after which the sorbent laden with reaction product settles in a sorbent collection zone.

In some embodiments, the liquid sorbent is cooled by means of a cooling device in the reaction space. In some embodiments, the cooling of the sorbent increases the number of available species; on the other hand, the lowering of the temperature in the reaction chamber has a positive influence on the equilibrium conversion. In some embodiments, the sorbent to be cooled by the cooling device in the region of the sorbent collection zone.

In some embodiments, the sorbent laden with the reaction product is passed off out of the reaction chamber and the reaction product is separated from the sorbent. The sorbent thus unladen can be recycled by being reintroduced into the reaction chamber.

In some embodiments, the laden sorbent is circulated by a circulation device in the region of the sorbent collection zone, in order to improve exchange with the cooling device.

FIG. 1 depicts a reactor 2 comprising a stirred tank reactor. This reactor 2 further comprises a reactant feed device 6 and a feed device 8 for sorbent 9. In a reaction chamber 4, reactants 7 and sorbent 9 are introduced. The reaction chamber 4 further comprises a catalyst space 20 for accommodating a catalyst 22. The reaction chamber 4 further comprises a sorption space 24, in which the sorbent 9 is located, e.g. in droplet form. The sorbent 9 settles continuously in the direction of a lower region 11, where there is a sorbent collection zone 12 located.

The text below gives further details of a typical reaction process which takes place in the reactor 2 or in the reaction chamber 4. The gaseous reactants 7, as already mentioned, are introduced into the reaction chamber 4, and they are passed to the location in the reaction chamber 4 at which the catalyst 20 is present. By the setting of suitable reaction conditions, tailored in each case to the corresponding reaction and/or corresponding reactants, there is an exothermic reaction (giving off heat) of the reactants over the catalyst to form liquid or gaseous reaction products 15. In a gas phase within the reactor, there is an increase in the temperature, with the possible consequence of deactivation mechanisms on the catalyst (boiling or sintering). The gas phase in the reactor here comprises not only gaseous reactants 7 but also possible gaseous reaction products 15. In a reaction arrangement of this kind, the reactants 7 will react maximally until the thermodynamically possible equilibrium conversion, which in certain reactions lies at low values. For example, the reaction of carbon dioxide and hydrogen to give methanol:

$$CO_2 + 3H_2 \rightarrow CH_3OH + H_2O \qquad \text{eq. 1}$$

is limited thermodynamically by a low equilibrium conversion under typical and economic reaction conditions. The typical reaction conditions for this are a pressure of 75 bar and a temperature of 250° C. As a result of the large amount of heat given off, in other words as a result of the release of energy during the reaction, the equilibrium conversion is lowered in this reaction, since the reaction temperature rises. It is therefore useful to remove the heat liberated by the reaction of the gas phase from the reaction chamber by means of suitable measures. The measures in question are addressed below.

An appropriate sorbent 9 here is, for example, an aqueous liquid, a heat transfer oil, a salt melt, or an ionic liquid which has a high heat capacity but an extremely low vapor pressure. In some embodiments, a mixture for a sorbent may comprise, for example, a mixture of a phosphonium NTf2 IL and an alkali metal or alkaline-earth metal NTf2 salt. An incomplete listing of suitable ionic liquids is given in table 1.

TABLE 1

Ionic liquids suitable for sorption (in some cases with admixture of salts)
Ionic liquid $P_{1444}$ NTf$_2$
$P_{66614}$ NTf$_2$
$N_{1888}$ NTf$_2$
Mixture of $P_{1444}$ NTf$_2$ and Li NTf$_2$
Mixture of $P_{1444}$ NTf$_2$ and Cs NTf$_2$
Mixture of $P_{1444}$ NTf$_2$ and Mg (NTf$_2$)$_2$
Mixture of $P_{1444}$ NTf$_2$ and Ca (NTf$_2$)$_2$
$P_{1444}$ MeSO$_4$ TABLE 1-continued Ionic liquids suitable for sorption (in some cases with admixture of salts)
Ionic liquid $P_{1444}$ $Me_2PO_4$
EMIM $NTf_2$
EMIM $MeSO_4$
$P_{1444}$ OTf
$P_{2444}$ $Et_2PO_4$ The sorbent is able to absorb the heat contained in the gas phase and therefore lower the temperature of the gas phase. This leads to a homogeneous distribution of temperature in the reaction zone (in the environment of the catalyst) and hence to at least effectively an isothermic behavior in the reaction chamber 4. This requires effective heat exchange of the reactants 7 with the absorbent 9.

The catalyst 21 and the sorbent 9 are as far as possible not to come into contact with one another, since such contact may adversely affect their stability and their functionality. For this reason, it is useful for the catalyst space 20 to be separated from the sorption space 24 by a gas-permeable element 26. This gas-permeable element 26 may be designed, for example, in the form of a metallic woven fabric or in the form of a membrane which is permeable to the corresponding gas phases. This makes it possible for the generally gaseous reactants 7 to penetrate through the gas-permeable element 26 and react at the catalyst surface to form the reaction products 15. Under the prevailing atmosphere, the reaction products 15 are likewise generally gaseous and they depart the catalyst space 20 through the corresponding element 26. After they have entered through the element 26 into the sorption space 24, they can be absorbed by the sorbent 9. The sorbent 9 laden with the reaction products 15 is referred to hereinafter as 9'.

FIG. 1 here shows an embodiment where the sorbent is cooled by a cooling device 13 directly within the reaction chamber 4 in a reactant collection zone 12. This cooling device 13 is designed so that it is arranged below a liquid level 14 of the sorbent collection zone 12. The cooling device 13 is therefore completely immersed in the sorbent in the collection zone 12, leading to more efficient cooling of the sorbent 9. In some embodiments, there is a circulating device 18, in the form of a stirring device 19, for example. The effect of this is that the heated sorbent 9' laden with the reaction products 15 blows continuously around the cooling device 13 in the region of the sorbent collection zone 12, and hence there is optimum heat exchange. As cooling device 13 it is possible to use heat exchangers disposed in the form of cassettes in the sorbent collection zone 12. In principle, however, other forms of design are also useful; for example, a cooling device 13 may be integrated directly in a wall of the reaction chamber 4.

In some embodiments, the heat can be taken off directly in the reactor 2 or in the reaction chamber 4 without heating in the reaction chamber 4 and therefore no reduced absorption capacity of the sorbent 9 for reaction products 15. A portion of the sorbent 9' laden with the reaction product 15, from the reactant collection zone 12, is subsequently removed from the reaction chamber 4 via a discharge device 10. The laden sorbent 9' is passed into a phase separator 28, in which the sorbent 9 is separated from the product 15. The product 15 is drawn off and collected otherwise. The unladen sorbent 9 is passed back to the feed device 8 for the sorbent 9, by way of a recycling device 16 which comprises a pump 17. The sorbent 9 recycled in this way passes back into the reaction chamber 4 and is ready to receive reaction products 15.

Figure 2:
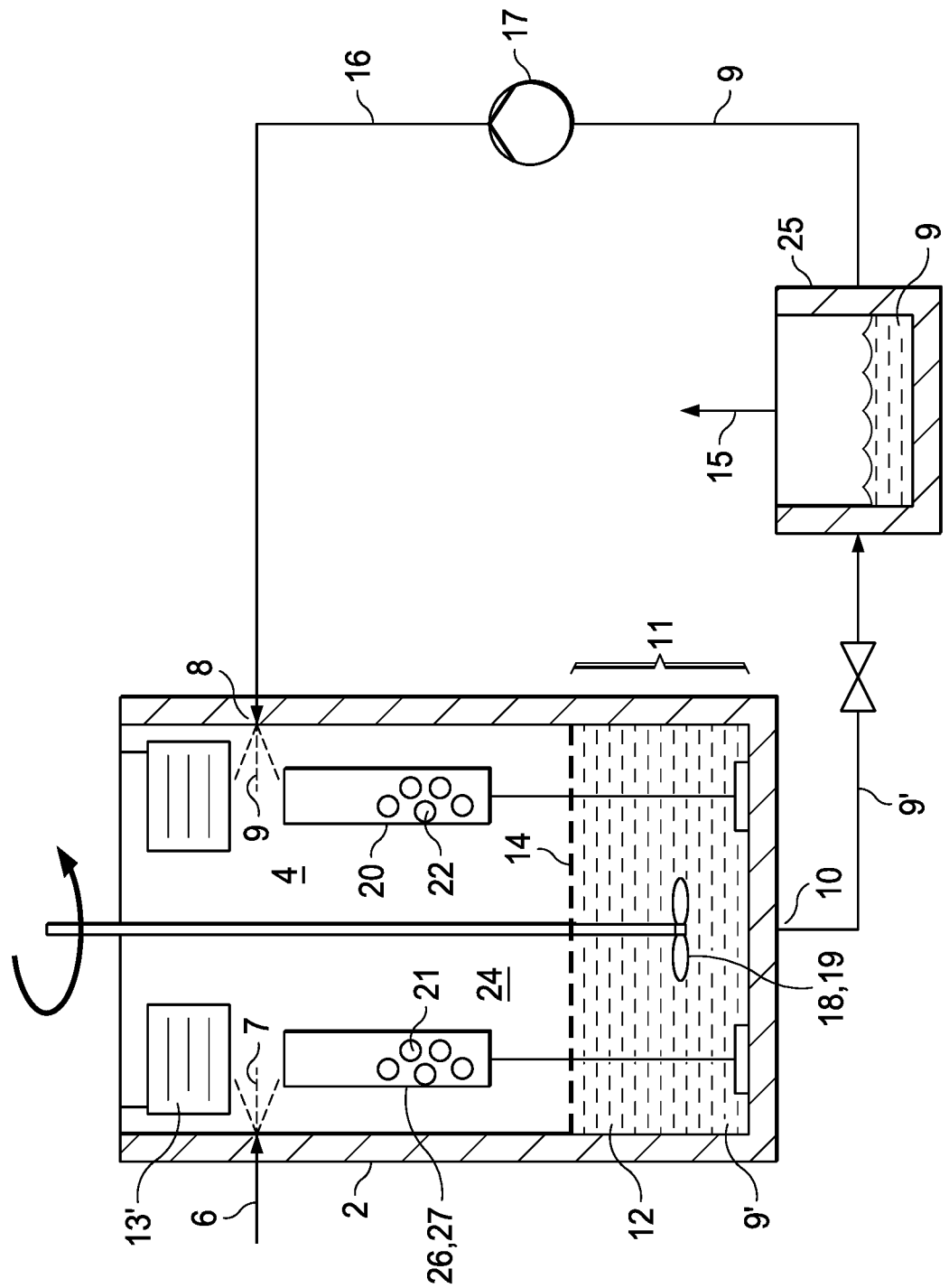
FIG. 2 shows a reactor analogous to the reactor of FIG. 1, where the sorbent is cooled outside the sorbent collection zone.

In some embodiments, such as that shown in FIG. 2, the cooling device 13' is not disposed, as depicted in FIG. 1, in the region of the sorbent collection zone 12, but instead in an upper region of the reaction chamber 4. In some embodiments, the cooling device 13' arranged at this location promotes the dissolution of reaction products 15 in the sorbent 9 and likewise promotes the condensation of the liquid products 15. In some embodiments, there is cooling of the reaction chamber 4 and hence of the entire atmospheric environment in the reaction chamber 4, with positive consequences for the reaction conditions and hence for the equilibrium conversion.

In some embodiments, the reactants 7 are introduced in gaseous form into the reaction chamber 4; alternatively, however, it is also possible for the reactants 7 to be introduced in a condensed phase, in other words in liquid form, into the reaction chamber 4. Reactants 7 may be fed in a liquid or supercritical state at a high fluid density to the reactor 2. Within the reactor, then, in the reaction chamber 4, an evaporation takes place, since under reaction conditions the reactants or the reactant are or is gaseous. The liquid reactants can be introduced at the location of the release of heat over the catalyst 22. In this case, local injection is employed—that is, a corresponding embodiment, not shown here, of the feed device 6 for reactants 7. In the case of the reaction according to equation 1 for the synthesis of methanol, in this case the carbon dioxide reactant may be added in liquid or supercritical form.

What is claimed is:

1. A reactor comprising:
    a reaction chamber having a lower region defining a sorbent collection zone;
    a first feed device supplying reactants to an upper portion of the reaction chamber above a level of a catalyst disposed in a catalyst space;
    a second feed device supplying a liquid sorbent to the upper portion of the reaction chamber above the level of the catalyst, the liquid sorbent flowing from the second feed device down to the sorbent collection zone under the effects of gravity;
    a discharge device connected to the sorbent collection zone for removing sorbent from the sorbent collection zone; and
    a cooling device disposed in the reaction chamber for cooling the sorbent before the sorbent is removed by the discharge device.

2. The reactor as claimed in claim 1, wherein the cooling device is disposed in the sorbent collection zone.

3. The reactor as claimed in claim 2, wherein the cooling device is disposed, in one operating state, below a liquid level of the sorbent in the reaction chamber.

4. The reactor as claimed in claim 1, further comprising a recycling device for recirculating the sorbent, the recycling device arranged between the discharge device and the second feed device.

5. The reactor as claimed in claim 1, further comprising a circulating device disposed in the sorbent collection zone.

6. The reactor as claimed in claim 1, wherein the reaction chamber comprises a sorption space.

7. The reactor as claimed in claim 1, wherein the reaction chamber comprises:
    a sorption space; and
    a gas-permeable element separating the catalyst space from the sorption space.

8. The reactor as claimed in claim 1, further comprising a phase separator arranged outside the reaction chamber for separating the sorbent from a reaction product;
   wherein discharge device feeds the phase separator.

9. The reactor as claimed in claim 4, wherein the recycling device comprises a phase separator for separating the sorbent from a reaction product.

10. A method for operating a reactor, the method comprising:
   feeding reactants into an upper portion of a reaction chamber;
   feeding a liquid ionic sorbent agent into the upper portion of the reaction chamber;
   exposing the reactants to a catalyst in the reaction chamber;
   converting the reactants to reaction products over a catalyst surface until an equilibrium situation is established;
   conveying the reaction products from the catalyst surface to the liquid sorbent and are absorbed thereby;
   wherein at least a portion of the sorbent laden with the reaction products settles in a sorbent collection zone in a lower portion of the reaction chamber, the laden sorbent flowing down to the sorbent collection zone under the effects of gravity; and
   cooling both the liquid sorbent and the at least a portion of the sorbent in the reaction chamber.

11. The method as claimed in claim 10, wherein the sorbent is cooled in the sorbent collection zone.

12. The method as claimed in claim 10, further comprising:
   removing the at least a portion of the sorbent laden with the reaction product from of the reaction chamber;
   separating the reaction product from the at least a portion of the sorbent to recover unladen sorbent; and
   recycling the unladen sorbent by reintroducing the unladen sorbent into the reaction chamber.

13. The method as claimed in claim 10, further comprising circulating the at least a portion of the sorbent within the sorbent collection zone.

* * * * *